United States Patent
Peyman

(10) Patent No.: US 8,554,296 B2
(45) Date of Patent: *Oct. 8, 2013

(54) PHOTOACOUSTIC MEASUREMENT OF ANALYTE CONCENTRATION IN THE EYE

(76) Inventor: Gholam A. Peyman, Sun City, AZ (US)

( * ) Notice: Subject to any disclaimer, the term of this patent is extended or adjusted under 35 U.S.C. 154(b) by 20 days.

This patent is subject to a terminal disclaimer.

(21) Appl. No.: 13/400,240

(22) Filed: Feb. 20, 2012

(65) Prior Publication Data

US 2012/0150013 A1 Jun. 14, 2012

Related U.S. Application Data

(63) Continuation-in-part of application No. 11/870,935, filed on Oct. 11, 2007, now Pat. No. 8,121,663, which is a continuation of application No. 11/323,232, filed on Dec. 30, 2005, now abandoned.

(60) Provisional application No. 60/727,078, filed on Oct. 14, 2005.

(51) Int. Cl.
A61B 5/1455 (2006.01)

(52) U.S. Cl.
USPC ............ 600/319; 600/310; 600/316; 600/322

(58) Field of Classification Search
USPC .................................... 600/310–344
See application file for complete search history.

(56) References Cited

U.S. PATENT DOCUMENTS

| | | |
|---|---|---|
| 3,958,560 A | 5/1976 | March |
| 3,963,019 A | 6/1976 | Quandt |
| 4,350,163 A | 9/1982 | Ford et al. |
| 4,556,293 A | 12/1985 | Burns et al. |
| 5,258,788 A | 11/1993 | Furuya et al. |
| 5,535,743 A | 7/1996 | Backhaus et al. |
| 5,553,617 A | 9/1996 | Barkenhagen |
| 5,560,356 A | 10/1996 | Peyman |
| 5,710,630 A | 1/1998 | Essenpreis et al. |
| 5,941,821 A | 8/1999 | Chou |
| 6,070,093 A | 5/2000 | Oosta et al. |
| 6,403,944 B1 | 6/2002 | MacKenzie et al. |
| 6,490,470 B1 | 12/2002 | Kruger |
| 6,609,015 B2 | 8/2003 | Lucassen et al. |
| 6,725,073 B1 | 4/2004 | Motamedi et al. |
| 6,846,288 B2 | 1/2005 | Nagar et al. |
| 2005/0190372 A1 | 9/2005 | Dogariu |

OTHER PUBLICATIONS

Levitz et al., Determination of optical scattering properties of highly-scattering media in optical coherence tomography images, Optics Express, vol. 12. No. 2 Jan. 2004.

Charters, Advance OCT opens way for 3-D retinal images, Ophthalmology Times, Aug. 2005.

Larin et al., Noninvasive Blood Glucose Monitoring with Optical Coherence Tomography, Diabetes Care, vol. 25, No. 12, Dec. 2002, p. 2263-2267.

(Continued)

Primary Examiner — Eric Winakur
Assistant Examiner — Marjan Fardanesh
(74) Attorney, Agent, or Firm — Thompson Hine LLP

(57) ABSTRACT

An in vivo determination of the presence or concentration of an endogenous or exogenous substance by photoacoustically assaying the substance in the eye and correlating the presence or concentration of the substance in the eye to the presence or concentration of the substance in the blood, without removing a tissue or fluid sample from the body for assay. The eye, unlike other body sites such as the skin, has a relatively constant pressure and temperature, providing an additional utility for the inventive method.

18 Claims, 1 Drawing Sheet

(56) References Cited

OTHER PUBLICATIONS

Larin et al., Specificity of noninvasive blood glucose sensing using optical coherence tomography technique: a polit study, Phy. Med. Biol., No. 28, p. 1371-1390, May 2003.

Khallil, Spectroscopic and Clinical Aspects of Noninvasive Glucose Measurements, Clinical Chemistry, vol. 45, No. 2, 1999, p. 165-177.

Rabinovitch et al., Noninvasive glucose monitoring of the aqueous humor of the eye: Part 1, Measurement of very small optical rotations. Diabetes Care, vol. 5, Issue 3, 1982, p. 254-258.

Fercher et al., Optical coherence tomography—principles and applications, 2003 Re. Prog. Phys. 66, p. 239-303, Jan. 2003.

Bonner, Diagnostic Devices of the New Millennium, An Optometric Odyssey, Spisode VIII, 23rd Annual diagnostic Technology Report, Aug. 2000.

Zvyagin et al., Refractive index tomography of turbid media by bifocal optical coherence refractometry, Optics Express, vol. 11, No. 25, Dec. 2003.

Glenn Research Center, *The Eye: Window to the Body*, John Glenn Biomedical Engineering Consortium, May 2002.

Arnaut & Pineiro, "Two-photon photoacoustic calorimetry and the absolute measurement of molar absorption coefficients of transient species in solution," Photochem. Photobiol. Sci., 2003, 2, 749-753.

Hung & Grabowski, "Listening to Reactive Intermediates: Application of Photoacoustic Calorimetry to Vitamin $B_{12}$ Compounds," J. Am. Chem. Soc. 1999, 121, 1359-1364.

Hagiwara et al., "Autofluorescence assessment of extracellular matrices of a cartilage-like tissue construct using a fluorescent image analyser," J. Tissue Eng Regen Med 2011; 5: 163-168.

PHOTOACOUSTIC MEASUREMENT OF ANALYTE CONCENTRATION IN THE EYE

CROSS REFERENCE TO RELATED APPLICATIONS

This application is a continuation-in-part of U.S. application Ser. No. 11/870,935, now U.S. Pat. No. 8,121,663 filed Oct. 11, 2007; which is a Continuation of U.S. application Ser. No. 11/323,232 filed Dec. 30, 2005 now abandoned; which claims priority to U.S. application Ser. No. 60/727,078 filed Oct. 14, 2005; each of which is incorporated by reference in its entirety herein.

FIELD OF THE INVENTION

The invention relates to a non-invasive, in-vivo method and a system for the determination of the concentration of a substance in different areas of the eye.

BACKGROUND OF THE INVENTION

Many medical diagnostic techniques project radiant energy into the body of an animal for testing for the existence of a biomedical disorder or condition. For example, the integrity of the skeletal structure may be examined by passing X-rays through the body. The dense bony material substantially blocks the passage of the X-rays, permitting a doctor or other medical care provider to visually inspect for fractures or other defects in the skeletal structure.

To examine the soft tissue of the body, other techniques are available. These include, among others, CAT scans and magnetic resonance imaging. Both project radiant energy onto the body for obtaining information about the physical structure of the body.

Further, measurement of the level of certain chemicals or compositions within the body is a diagnostic test of particular interest. Radiant energy may be used in these applications as passage of the radiant energy through particular chemicals or compositions often alters the radiant energy in a manner that can be measured and analyzed. For example, the monitoring of the glucose level of the blood is of particular importance to diabetics.

One method of measuring the person's glucose involves projecting polarized radiation onto the body and measuring the optical rotation of the radiation that passes through the body. This optical rotation corresponds to the concentration of the glucose within the body. However, to be effective in measuring the concentration of a component the radiation must be passed through a relatively thin area of the body.

In another example, Larin et al. (*Diabetes Care*, Vol. 25, No. 12 pp. 2263-2267) describes a method of the noninvasive blood glucose measurement with optical coherence tomography. The glucose concentration was determined by the slope of the OCT signals. A calibration curve, however, is needed for the glucose concentration.

U.S. Pat. No. 6,403,944, the disclosure of which is incorporated herein by reference, uses a photoacoustic effect for glucose measurement. Pulses of light at a wavelength for which light is absorbed by glucose (e.g., 1000-1800 nm) are directed from a light guide into soft tissue of the person's body, such as a fingertip. The light pulses are typically focused to a relatively small focal region inside the body part and light from the light pulses is absorbed by glucose and converted to acoustic energy. The kinetic energy causes temperature and pressure of the absorbing tissue region to increase and generates acoustic waves, known as "photoacoustic waves", that radiate out from the absorbing tissue. An acoustic sensor in contact with the soft tissue senses the photoacoustic waves, and the intensity of those waves is used to assay the glucose.

U.S. Pat. No. 5,941,821, which is hereby incorporated herein by reference, describes another glucometer that uses a photoacoustic effect. This device illuminates the skin surface with modulating light at a carrier wavelength at which glucose absorbs light. Glucose in the blood and interstitial fluid near the tissue surface, absorbs the light and converts the absorbed energy to kinetic energy that heats the tissue. Temperature of the tissue increases and decreases cyclically in cadence with the modulation of the light. The alternate heating and cooling of the tissue results in periodic heating of air in contact with the surface of the illuminated region, which generates sound waves in the air. A microphone measures these sound waves which are used to determine a concentration of glucose.

A third example is described by U.S. Pat. No. 6,846,288, owned by Glucon, Inc., which is hereby incorporated herein in its entirety. There, a region of interest is illuminated with at least one pulse of radiation having a wavelength at which the radiation is absorbed, to generate a change in acoustic properties of the region. Then, ultrasound is transmitted so that it is incident on the region. Changes in the incident ultrasound are measured, to determine an absorption coefficient for the radiation, which can be converted to a concentration of glucose.

Unfortunately, these approaches all suffer from a number of drawbacks. Specifically, light is scattered by body tissue, and thus even in the '944 patent where light is focused to a region inside the body, the location and size of the absorbing tissue region are not accurately known. Furthermore, the generated photoacoustic effect in soft tissue, and thus measurements of the patient's glucose levels, are not necessarily the result only of glucose concentration in the blood. Characteristics of the absorbing tissue region, such as density of blood vessels therein, can affect concentration of glucose in the absorbing region and often are not accurately known. Furthermore, calibration must account for the nature of the body part and its size, skin color, skin condition, body fat and other factors that affect light absorption, transmission and heating of soft tissue. Measurements of blood glucose levels can therefore be affected by unknown variables that substantially compromise the reliability of those measurements.

The above techniques and disclosures discuss applications on the soft tissue of the body via the skin. Other techniques have projected radiant energy through the cornea and aqueous humor of the eye to measure glucose. The concentration of glucose and oxygen in the cornea and aqueous humor reflects the concentration generally throughout the body, and so such measurements are diagnostically useful. However, several problems are associated with these techniques.

For example, in Quandt U.S. Pat. No. 3,963,019, radiant energy is projected into the eye and reflected off the iris. The reflected radiation is detected, and the optical rotation caused by passage of the reflected radiation through the cornea and aqueous humor is determined. However, this method suffers from poor sensitivity, in part because it relies on reflecting the radiant energy off the iris.

Other attempts, as shown in March U.S. Pat. No. 3,958,560 and March U.S. Pat. No. 4,014,321, project the radiant energy at a shallow angle into the cornea on one side of the eye, through the aqueous humor, and out the cornea on the opposing side of the eye. Although this test is able to achieve high accuracy, it is difficult to administer because of the shallow angle at which the radiant energy must be passed through the eye.

U.S. Pat. No. 5,560,356 describes a system that uses an implanted reflective device in the anterior chamber or cornea of the eye. The incident polarized beam of radiation is projected into through the aqueous humor and/or cornea and is refracted or optically rotated in an amount that is proportional to the concentration of glucose or other substance present. The altered beam is reflected to a receiver by an implanted reflective device and processed to determine the glucose concentration.

All of these methods, however, measure glucose in only one area of the eye at any one time, and each relies upon optical methods for transmission and return of information. It would be advantages to measure concentration of glucose or another substance without these limitations.

SUMMARY OF THE INVENTION

An in vivo determination of the presence or concentration of an endogenous or exogenous substance by photoacoustically assaying the substance in the eye and correlating the presence or concentration of the substance in the eye to the presence or concentration of the substance in the blood, without removing a tissue or fluid sample from the body for assay. The inventive method using photoacoustic spectroscopy is applicable to any fluid, liquid or gas, in the eye. The eye, unlike other body sites such as the skin, has a relatively constant pressure and temperature. This is one reason the inventive method is useful.

In one aspect, the invention features a method and device for measuring blood concentration of a substance such as but not limited to glucose in the aqueous humor by a method that avoids the drawbacks of the above-described approaches. As used herein, the terms "substance" and "analyte" are used interchangeably and synonymously. It is, however, recognized by the skilled person that the term "substance" is recognized to be either externally administered (e.g., an antibiotic substance administered by e.g., injection, topical application, etc.), and/or non-physiologic (e.g., a nanoparticle, a quantum dot, a nanoparticle conjugate, a quantum dot conjugate, etc.). The term "analyte" is recognized to be naturally present in the body (e.g., a level of glucose), whether by normal physiology, by metabolism, etc., and whether present or generated locally in the eye, or whether they are present transiently in the eye (e.g., present in the circulation in blood, plasma, circulating cells, etc.). Again, these distinctions and definitions are used for clarity, but the terms "substance" and "analyte" are used interchangeably.

In one aspect, the invention features methods and devices for measuring concentration of a substance in body fluids such as interstitial and other fluids that avoids the drawbacks of the above-described approaches.

The basis of photoacoustic spectroscopy is detecting generalization of acoustic sound by absorption of energy (electromagnetic or light) by a substance. Sounds produced by different wavelengths creates a photoacoustic spectrum specific to various component of a composite material. The material can be a liquid or a gas. This is done by directing a spectrum of wavelengths of light (ultraviolet (UV) to near infrared (NIR)) sequentially at one place or at multiple places inside the eye. The information can be stored, imaged, and analyzed producing a photoacoustic spectroscopy from the content of the eye cavity. The basic technology is as described: an intense laser or diode laser measures the intensity of light that generates the proportional sound wave. This requires a prism or diffraction grating to record the intensity of the wavelengths, interferometer and Fourier transform instrument etc.), a microphone with lock-in amplifier, signal processing with a digital signal processor, or integrated micro-machined photoacoustic instruments, et., as known in the art.

Specifically, this method involves illuminating the fluid (e.g., aqueous humor) with a light source at a frequency that is absorbed by the substance to the measured, and then sensing photoacoustically generated sound waves originated within the fluid (e.g., aqueous humor) as a consequence of illumination by the light source. The blood concentration can be estimated from the amplitude of the sound waves.

This method has the advantage that the radiant energy used to stimulate the photoacoustic response need not pass through soft tissue, but rather passes through a relatively clear and optically transmissive media. Furthermore, this method has the advantage that light need not be reflected or otherwise directed to a detector for the measurement to be accomplished, as the measurement is accomplished from acoustic, rather than electromagnetic, response signals.

Although it has been known to use a photoacoustic method to measure blood glucose in opaque tissue such as through the skin, use of this method in the aqueous humor and other fluids is believed to be new, and has distinct advantages over these known applications for the reason that the aqueous humor and other fluids that are relatively transparent, and thus permit focused illumination over a larger range of tissue structure than could be achieved in opaque areas. At the same time, the glucose concentration within the aqueous humor and other fluids is reflective of the body as a whole and thus the quality of the measurement is not compromised.

BRIEF DESCRIPTION OF THE DRAWINGS

The invention will be described with reference to the following drawings, in which.

DETAILED DESCRIPTION OF THE INVENTION

Figure 1:
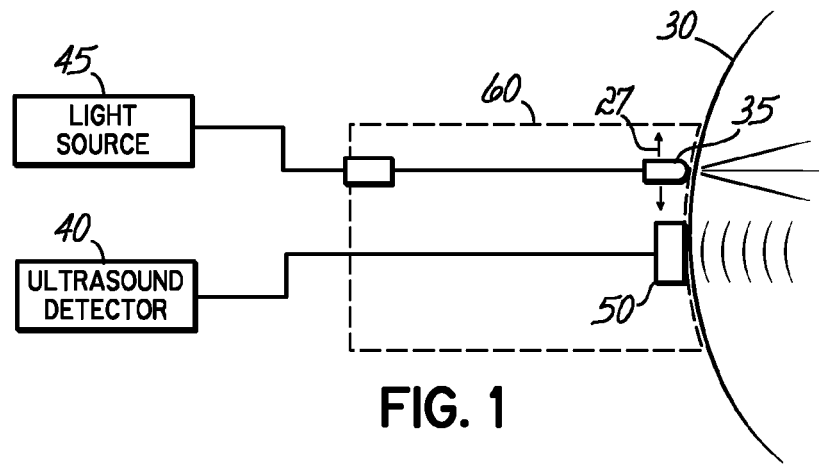
FIG. 1 illustrates a first embodiment of the invention for measuring photoacoustic signals developed within the eye in response to illuminating light.

In one embodiment of the inventive system, the glucose concentration is measured in the eye, by a photoacoustic assay such as that described in U.S. Pat. No. 6,846,288 (e.g. at col. 13 line 62 to col. 18 line 49) or in U.S. Pat. No. 6,403,944, each of which is incorporated by reference in their entirety.

In one embodiment non-glucose substances, also referred to as analytes, that are present in the eye are also measured by a photoacoustic assay. For example, photoacoustic signals for methylcobalamin and methylcobinamide of the $B_{12}$ family of compounds, were measured, as described in Hung and Grabowski, J. Am. Chem. Soc. 121 (1999) 1359, which is expressly incorporated by reference herein in its entirety. These substances include, in addition to glucose and the vitamin $B_{12}$ family, endogenous substances such as glycosylated hemoglobin, oxygenated hemoglobin, non-oxygenated hemoglobin, oxygen, urea nitrogen (i.e., BUN), creatinine, bilirubin and its conjugates and metabolites (e.g., biliverdin, etc.), vitamins (e.g. vitamin A, vitamin D, vitamin C, the vitamin $B_1$ family), proteins, cytokines, opsins, growth factors, hormones and hormone metabolites, etc. These substances also include antibiotics, anti-fungals, anti-virals, and anti-proliferative agents, any of which may be in various formulations and conjugates, e.g., nanoparticles, quantum dots, and quantum dot conjugates, etc. For example, hemoglobin oxygen saturation/concentration were assayed by photoacoustic microscopy/tomography by, respectively, by Zhang et al., Applied Physics Letters 90 (2007) 053901-1-3; and Wang et al. Journal of Biomedical Optics 11 (2006) 024015-1-9.

Any reference to substances or analytes that are present in the eye includes substances that are present at or in any anatomical site or portion of any anatomical site in the eye, portion of the eye, compartment or compartments of the eye whether discreet, directly interconnected, or indirectly interconnected. Examples include, but are not limited to, a surface of the retina, a surface of the choroid, etc. Such sites contain other structures and tissues, e.g., vessels; fluid-containing sites, e.g., aqueous humor, vitreous humor; spaces between substructures and/or layers, e.g., within areas of the lens, within the retina, under the retina (e.g., sub-retinal fluid), within or between the iris and lens, sclera, choroid, etc.; blood vessels permeating throughout the eye; interstitial fluid, etc.

If the analytes are conjugated, the conjugates include, but are not limited to, nanoparticles, liposomes, micelles, nanocarbon particles, etc.

Analytes measurable by the inventive method include substances that naturally occur in blood (e.g., circulating in vessels in the eye) and substances that are produced as a result of metabolism/biotransformation.

Analytes measurable by the inventive method can be present in any liquid or gaseous physical form. In one embodiment, the analyte is present in a solution. In one embodiment, the analyte is present in a suspension. In one embodiment, the analyte is present in a gas (e.g., oxygen, $CO_2$). In one embodiment, the analyte is present as a radical (e.g., hydroxyl radical, superoxide radical, etc.).

Substances may be administered to a patient by any route, including but not limited to topical administration (creams, eye drops, salves, gels, etc.), injection which includes injection into the circulatory system (e.g., intravenous injection) and injection into the eye (e.g., intravitreal injection, subretinal injection, etc.). Administration may be to any area (e.g., front of the eye, back of the eye), or portion of the eye (choroid, sclera, retina, etc.).

The inventive method is applicable to any substance or analyte that absorbs energy from a light source and generates a photoacoustic wave or signal or sound wave pulse as a result of the absorbed energy. Substances include, without limitation, both endogenous and exogenous substances listed above that absorb energy and generate a resulting photoacoustic wave, signal, or sound wave pulse as described in, e.g., Hung and Grabowski, J. Am. Chem. Soc. 121 (1999) 1359; Edney and Walsh, Applied Optics 40 (2001) 6381-6388; Chandra et al., Pharmaceutical Research 28, 279-291; Arnaut and Pineiro, Photochemical & Photobiological Sciences 2 (2003) 749-753; Hagiwara et al. Journal of Tissue Engineering and Regenerative Medicine 5 (2011) 163-168; each of which is expressly incorporated by reference in its entirety.

As shown in FIG. 1, the probe module 60 includes an objective lens structure 35, which is coupled to a light source 45 via a fiber optic connection or other light transmitter. Light source 45 provides light at a wavelength which is preferentially absorbed by glucose. Alternatively, the light source may be incorporated into the probe module 60.

The light source 45 may be a laser, laser diode or superluminescent diode (SLD), as appropriate for generating the desired light wavelength and intensity. The light may be delivered as pulses or as modulated radiation.

The probe module 60 further contains an ultrasound transducer 50 to detect the photoacoustic waves that are generated as a result of the absorption of energy from the light emitted by the objective lens structure 35. The ultrasound transducer 50 is in contact with the eye 30 or an eyelid drawn over the eye. As light is delivered as pulses or as modulated radiation (as elaborated in the above-referenced U.S. Pat. Nos. 6,846,288 and 6,403,944), pulses or modulating acoustic signals are generated and returned to the ultrasound transducer 50 in probe module 60. As noted, it is expected that substantially superior results, in repeatability and ease of calibration, will be achieved in the eye than are achieved in soft tissue as proposed by the '288 and '944 patents.

It will be appreciated that localization of the source of photoacoustic signals may be achieved in various manners. First, localization may be accomplished by directing the beam from objective lens structure 35 in specific directions, by moving that structure with micromechanical actuators as shown diagrammatically at 27 in FIG. 1, thus targeting a particular line of points in the eye. Furthermore, by suitable optics included in objective lens structure 35, the focal point of the emitted light may be moved within the eye to a desired point, such as a point along the retina vasculature, to selectively generate acoustic signals at that desired point. Because the eye is optically transmissive relative to soft tissue, beam focusing and beam directing are likely to be more accurately performed in the eye, than is the case is soft tissue elsewhere in the body.

To further assist in directionally capturing the photoacoustic signals generated within the eye, a directional transducer array may be used as transducer 50, to control the directionality of reception of ultrasonic energy, thus further localizing upon a desired source of thermoacoustic signals. Thus, by targeting the focal point of the illuminating light, and also directionally targeting the reception of ultrasonic signals by the transducer array, thermoacoustic signals from a particular location, such as along the retina, may be specifically targeted.

Mapping of patient eye structures is useful for analysis of macular edema, macular holes, glaucoma, various retinal diseases, diabetic retinopathy, retinitis, ischemic retina of the optic nerve, neuroophthalmology, the anterior segment, and normal eye conditions. For such applications, it will be appreciated that the ultrasound transducer 50 may transmit and receive ultrasound waves; when transducer 50 transmits waves, reflected ultrasound waves may be used for imaging of eye structures, as is a known use of ultrasound for imaging. Eye structures localized with ultrasound may then be targeted by the optical system and transducer 50 for photoacoustic analysis. The combined use of sensors for ultrasound imaging and thermoacoustic reception is explained further in U.S. Pat. No. 6,490,470, which is hereby incorporated herein by reference in its entirety.

It will also be appreciated that the apparatus shown in FIG. 1 may be adapted to analyze glucose with reflected or transmitted ultrasound, i.e., ultrasound that passes through an irradiated area in the eye may be captured and its properties analyzed to determine glucose concentration, as discussed in U.S. Pat. No. 6,846,288. For such an application, an ultrasonically reflective structure may be utilized to reflect ultrasound transmitted into the eye so that the reflected ultrasound may be analyzed. The skull may be utilized for this purpose, or another reflector may be temporarily positioned within the eye socket for this purpose. Alternatively, an ultrasound emitter may be placed adjacent to the eye within the eye socket to generate ultrasound that may be received by a directionally-oriented receiver after passing through an area subject to illumination by light source 45.

Figure 2:
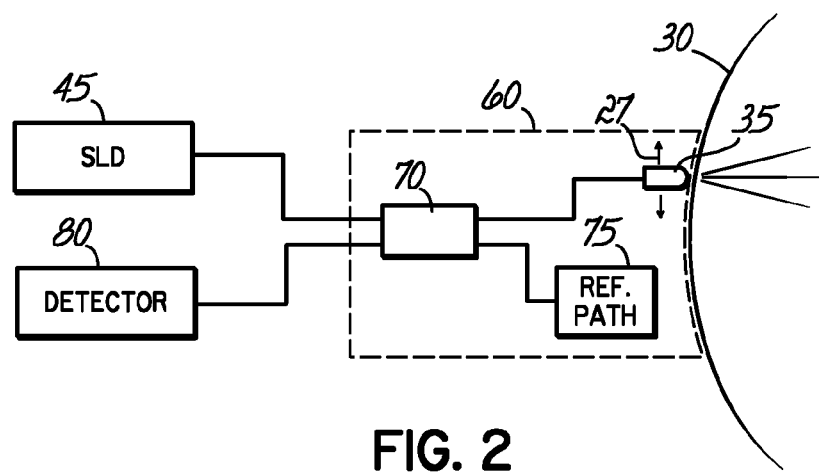
FIG. 2 illustrates an interferometry method for detecting glucose concentration in the eye.

In alternative embodiments of the invention, glucose concentrations within the eye may be measured in conjunction with a reflection interferometry method, such as a short coherence reflection interferometry method as generally described (for soft tissue) in U.S. Pat. No. 5,710,630(Col. 10, line 20 to Col. 14, line 27). In this system, as shown in FIG. 2, the probe contains a superluminescent diode (SLD) light source 45 that transmits a wavelength of, e.g., 1300 nm, delivered to the imaging site through optical fiber and a coupler 70, into the eye 30. Light is also coupled from coupler 70 to a reference path 75, from which it is reflected to create interferometry with the reflections from the eye 30 at a photodetector 80. Movement of the objective lens 35 within the probe 60 as shown at 27 permits illumination of specific eye features. The characteristics thereof may then be detected from the changing interferometry between the reflected light received from lens 35 and reference path 75, as described in U.S. Pat. No. 5,710,630. By using a low-coherence-length light source 45 and measuring the interference between light backscattered from a tissue and from a mirror in the reference path 75, the distance and magnitude of optical scattering within the tissue is measured.

Figure 3:
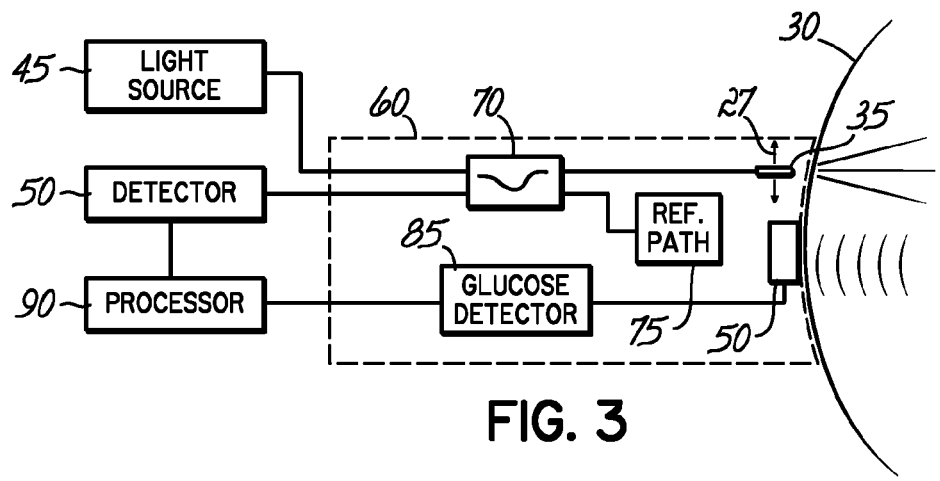
FIG. 3 illustrates a combined interferometry and photoacoustic system for detecting glucose concentrations at particular locations in the eye.

In a combined photoacoustic and interferometric system as illustrated in FIG. 3, the optical interferometry section generates light waves that reflect off the internal microstructure and also cause localized photoacoustic signal generation. Interferometric techniques extract the reflected optical signals from the infrared light and the output, measured by an interferometer, is processed to produce glucose measurements as well as potentially cross sectional or 3-dimensional images of the target site.

In this combined embodiment, probe module 60 also includes an ultrasound transducer 50 and glucose detector system 85 of the kind discussed with reference to FIG. 1. A processor 90 attached to interferometry detector 50 and to glucose detector 85 combines the resulting signals from each (FIG. 3). Scanning the light beam across the tissue produces a cross-sectional image by the signal processor 90, while processor 90 records the axial reflectance profiles at each transverse position. Processor 90 also records glucose measurements at each location generated by inteferometric methods and from photoacoustic data generated in response to light illumination. The result is a multi-dimensional representation of the optical backscattering of the tissue's cross-section, which displays as a gray-scale or false-color image, and a superimposable measure of glucose.

In one embodiment, a concentration gradient of a substance or analyte from the back of the eye to the front of the eye, or from the front of the eye to the back of the eye, is determined. This may be accomplished by a plurality of incremental measurements throughout a trajectory from the back of the eye to the front of the eye, or from the front of the eye to the back of the eye, resulting in an assay that results in an entire concentration gradient of the substance being assayed. Measurements, locations, intervals, etc. may be set using commercially available software configured to the photoacoustic sensor. For example, a user interface can allow the user to set a plurality of measurements at a plurality of times and/or locations in the eye, and a module manager can administer or control the illumination, detection, etc. An integrated system can analyze the data received and correlate it to a result in a concentration gradient.

Any of the substances previously described may be conjugated to nanoparticles, quantum dots, and measure by a photoacoustic assay. For example, Chandra et al. cited above and incorporated by reference, employ biocompatible cinnamon coated gold nanoparticles, using index of refraction changes in the liquid medium within which photoacoustic waves are propagated, thereby changing the reflectance of a laser probe beam. Pol et al. (Chem. Mater. 15 (2003) 1111-1118, and expressly incorporated by reference herein in its entirety), employ gold nanoparticles deposited on silica spheres. Such methods may be used, as modified if needed, as known to one skilled in the art.

In one embodiment, the substance (analyte) is simultaneously assayed and imaged to assess presence, quantity, and location. In this embodiment, imaging is performed by methods known in the art, including but not limited to magnetic resonance imaging (MRI), fluorescent imaging using a fluorophore, positron emission tomography (PET) imaging, ultrasound (US) imaging, optical coherence tomography (OCT), etc. In OCT, the acoustic optical signal depends upon the mechanical response of the tissue being assessed to the applied energy source used. One non-limiting disclosure of OCT imaging methods that may be used with the inventive photoacoustic methods is found in Edney and Walsh, Applied Optics 40 (34) 2001, 6381-6388). One non-limiting disclosure of OCT imaging uses a Mach-Zehnder interferometer in a two- or three-dimensional format to detect small changes in the free propagating light after a light pulse has triggered a photoacoustic sound; minute phase changes are created and detected.

While various embodiments have been chosen to illustrate the invention, it will be understood by those skilled in the art that various modifications can be made without departing from the spirit and scope of the invention as defined in the following claims.

What is claimed is:

1. A method of measuring the blood concentration of a liquid or gaseous substance within a fluid present in an eye, the method comprising
    illuminating the fluid present in the eye with a light source at a frequency that is absorbed by the liquid or gaseous substance to be measured,
    sensing only photoacoustically generated pulses or modulating acoustic signals originated within the liquid or gaseous fluid as a consequence of illumination by the light source, without light being reflected or otherwise directed to a detector,
    estimating blood concentration of the liquid or gaseous substance from an amplitude of received pulses or modulating acoustic signals, and
    displaying the estimated blood concentration.

2. The method of claim 1 further comprising providing an additional, non-photoacoustic, detector to image a location of the substance.

3. The method of claim 2 wherein the substance is imaged by optical coherence tomography.

4. The method of claim 1 where the substance is generated locally in the eye, or is transiently present in the eye from the circulatory system.

5. The method of claim 1 where the substance is externally administered to the eye.

6. The method of claim 1 further comprising using the light source to determine a concentration gradient of the substance from the front of the eye to the back of the eye, or from the back of the eye to the front of the eye.

7. The method of claim 1 where the substance is present in circulating blood cells.

8. The method of claim 7 where the substance is conjugated to a nanoparticle or to a quantum dot.

9. The method of claim 1 where the substance is selected from the group consisting of an antibiotic, an anti-viral agent, an anti-fungal agent, an anti-proliferative agent, an immunosuppressant, a cytokine, a hormone, and combinations thereof.

10. The method of claim 1 wherein the light source is a laser.

11. The method of claim 1 where the light source is a superluminescent diode.

12. The method of claim 1 where the illuminating with the light source comprises delivering pulsed light is delivered as pulses.

13. The method of claim 1 where the illuminating with the light source comprises delivering is delivered as modulated radiation.

14. The method of claim 1 where the received sensed acoustic signal is ultrasound.

15. The method of claim 1 where the substances are endogenous substances.

16. The method of claim 15 where the substances are selected from the group consisting of glycosylated hemoglobin, oxygenated hemoglobin, non-oxygenated hemoglobin, oxygen and oxygen radicals, urea nitrogen (BUN), creatinine, bilirubin and its conjugates and metabolites (e.g., biliverdin, etc.), vitamins (e.g. vitamin A, vitamin D, vitamin C, the vitamin $B_1$ family), proteins, cytokines, opsins, growth factors, hormones and hormone metabolites, and combinations thereof.

17. The method of claim 1 where the substances are exogenous substances.

18. The method of claim 17 where the substances are selected from the group consisting of antibiotics, anti-fungals, anti-virals, anti-proliferative agents, formulations and conjugates (e.g., nanoparticles, quantum dots, and quantum dot conjugates, etc.) thereof, and combinations thereof.

* * * * *